(12) United States Patent
Pesce

(10) Patent No.: US 11,085,058 B2
(45) Date of Patent: Aug. 10, 2021

(54) ANAEROBIC PROCESS FOR PRODUCING BIOGAS WITH A HIGH METHANE CONTENT BY MEANS OF THE BIODIGESTION OF ORGANIC WASTE

(71) Applicant: G-Meta Consultoria, Participações e Serviços LTDA, Rio de Janeiro (BR)

(72) Inventor: Luciano Pesce, Rio de Janeiro (BR)

(73) Assignees: G-META CONSULTORIA, PARTICIPAÇÕES E SERVIÇOS LTDA, Rio de Janeiro (BR); BIO-TRONIC ENERGY CO. LLC, Berkeley, CA (US)

( * ) Notice: Subject to any disclaimer, the term of this patent is extended or adjusted under 35 U.S.C. 154(b) by 0 days.

(21) Appl. No.: 14/373,094

(22) PCT Filed: Feb. 25, 2013

(86) PCT No.: PCT/BR2013/000051
§ 371 (c)(1),
(2) Date: Jul. 18, 2014

(87) PCT Pub. No.: WO2013/126977
PCT Pub. Date: Sep. 6, 2013

(65) Prior Publication Data
US 2015/0017697 A1    Jan. 15, 2015

(30) Foreign Application Priority Data
Mar. 2, 2012   (BR) .......................... 1020120047500

(51) Int. Cl.
*C12P 5/02* (2006.01)
*C12M 1/107* (2006.01)
*C12M 1/36* (2006.01)

(52) U.S. Cl.
CPC ............ *C12P 5/023* (2013.01); *C12M 21/04* (2013.01); *C12M 41/48* (2013.01); *Y02E 50/30* (2013.01)

(58) Field of Classification Search
None
See application file for complete search history.

(56) References Cited

U.S. PATENT DOCUMENTS

| | | | | | |
|---|---|---|---|---|---|
| 4,568,464 | A | * | 2/1986 | Blay | C02F 3/006 210/143 |
| 4,885,094 | A | * | 12/1989 | Srinivasan | C02F 3/1242 210/610 |
| 5,248,423 | A | * | 9/1993 | Moletta | C02F 3/006 210/614 |
| 5,529,692 | A | * | 6/1996 | Kubler | C02F 3/006 210/603 |
| 6,673,243 | B2 | * | 1/2004 | Srinivasan | C02F 3/284 210/532.2 |

FOREIGN PATENT DOCUMENTS

| | | |
|---|---|---|
| BR | 8502073-7 | 5/2007 |
| BR | PI 0600734-1 | 11/2007 |
| BR | PI 0617206-7 | 7/2011 |
| BR | PI 000529-3 | 10/2011 |
| CN | 1071899 * | 5/1993 |
| EP | 1236688 A1 | 9/2002 |
| EP | 2 248 886 A2 | 11/2010 |
| WO | 2006124781 A2 | 11/2006 |

OTHER PUBLICATIONS

Irini Angelidaki, Lars Elegaard, Birgitte K. Ahring; Bioconversion of Complex Substrates to Biogas; Biotechnology and Bioengineering, vol. 63, No. 3, May 5, 1999; Technical University of Denmark, 1998; Denmark.

H. Bouallagui, H. Landheb, E. Ben Romdan, B. Rachdi, M. Hamdi; Improvement of fruit and vegetable waste anaerobic digestion performance and stability with co-substrates addition; Laboratory of Microbial Ecology and Technology, National Institute of Applied Sciences and Technology, 2008, Tunisia.

Lopo José Infante da Câmara Lopo Carvalho; Avaliação Do Potencial de Produção de Biogás a Partir de Biomassa Proveniente de Culturas Dedicadas e de Lamas de Etari; Instituto Superior de Agronomia, Lisbon, 2010; Portugal.

Daniele Olmetto; Co-Digestione Anaerobica di Fanghi di Depurazione e Frazione Organica Dei R. , U.; Università di Bologna; 2007, Italy.

European Patent Office, Communication Under Rule 71(3) EPC dated Jan. 23, 2020 regarding the European Patent Application No. 13754168.6-1132, which is the European counterpart patent application of the U.S. Appl. No. 14/373,094.

European Patent Office, Communication Pursuant to Article 94(3) EPC dated Apr. 6, 2018 regarding the European Patent Application No. 13754168.6-1132, which is the European counterpart patent application of the U.S. Appl. No. 14/373,094.

* cited by examiner

*Primary Examiner* — Vera Afremova
(74) *Attorney, Agent, or Firm* — Li & Cai Intellectual Property (USA) Office

(57) ABSTRACT

This invention is about a process of increased Biogas (9) production, with high methane content, in anaerobic biodigestion plants, with production of electric (11) and thermal energy. The process is based upon biotechnologies, hardware and software specifically developed for this aim. One or more Devices for the Acceleration (4) of autochthon methanogenic bacteria multiplication, originally contained in the Organic Wastes (1), collect a portion of the biological material from the Anaerobic Biodigester (3) and, successively, gives it back at a higher rate, with its methanogenic bacteria population remarkably multiplied. The increase and stabilization of the reproduction and nutrition of these bacterial strains allows the increase of the biogas produced in the Anaerobic Biodigester (3) along with the percentage of methane contained in this very Biogas (9). The process is managed by an automation Expert System (5) which controls the biological, chemical and physical variables and that supervises the Automation and Control System (6) of the plant, providing commands and recipes also for the Compost (7) production system and for the Waste Water Treatment and Slurry Separation (8).

5 Claims, 3 Drawing Sheets

ANAEROBIC PROCESS FOR PRODUCING BIOGAS WITH A HIGH METHANE CONTENT BY MEANS OF THE BIODIGESTION OF ORGANIC WASTE

The invention refers to a process of production of biogas with high methane content in anaerobic biodigestion plants. The biogas may successively be employed in the generation of electric and thermal energy.

The process is based upon the use of biotechnologies, hardware and software specifically developed for this aim. The system stimulates and stabilizes biologically the production of autochthon methanogenic bacteria, originally contained in the wastes to be treated. The increase and stabilization in the reproduction and nutrition of these bacterial strains allows the increase in quantity of the biogas produced and of the percentage of methane contained in this very biogas. The process is managed by an automation expert system which controls the biological, chemical and physical variables for the result.

STATE OF THE ART

The process of anaerobic biodigestion is widely known, studied and employed since the antiquity, mainly in the treatment of civil sewage, in agriculture, cattle and pig breeding. In most applications it is applied in the sector of breeding, to treat cattle and pig manure. For each waste we have a potentiality of production of biogas, according to the percentage of volatile solids contained in that specific waste. Literature presents several tables about that, expressing the potentiality in terms of cubic meters of biogas produced for ton of waste processed ($m^3$/ton).

Percentage of methane contained in the biogas is normally expressed within a range 55% to 70%. Actually the higher level is rarely achieved due to the difficulty in controlling the process, which develops partly in a spontaneous way, reaching an average 70% of its potential during the time needed for the biodigestion (on average 30 to 40 days). Anaerobic biodigestion is nowadays considered a sustainable way to dispose of wastes, producing a certain amount of energy.

Several systems have been developed and patented too, depending on their process technologies, mainly about the dry, semi-dry, wet or particular state in which the organic wastes are processed in the digesters. Independently of the technological progresses, what has been considered during years of research and applications is mainly related to the disposal of organic polluting wastes, as a primary purpose of the plants, remaining the energy production a secondary aim.

The main achievements and improvements for the production of energy are related with:

1. Increase of bacterial activity through the addition in the digesters of organic material different from the basic substrate, frequently from agriculture (ex. corn).

2. Addition of nutrients, through a dosing system with timer, for compensating the C:N:P balance (Carbon, Nitrogen and Phosphorus).

3. Addition of enzymes, bacteria or biotechnological products imported from other countries, mainly U.S.A.

4. Automation Systems concerning only the mechanical and electronic components of the plants (automation, instruments, pumps, throttles, motors and so on).

REFERENCES a) Bibliography

ANGELIDAKI, I.; Ellegaard, L. & Ahring, B. K., (1999) A comprehensive model of anaerobic bioconversion of complex substrates to biogas, Biotechnology and Bioengineering, 63: 363-372

BOUALLAGUI, H.; Landheb H.; Ben Romdan, E.; Rachdi, B. & Hamdi, M. (2009) Improvement of fruit and vegetable waste anaerobic digestion performance and stability with co-substrates addition, Journal of Environmental Management, 90: 1844-1849

BRAUN, R.; Weiland, P. & Wellinger, A. (2009) Biogas from Energy Crop Digestion, IEA Bioenergy, Task 37

FERNANDO LUCIANO MERLI DO AMARAL (2004) Biodigestão dos resíduos sólidos urbanos: um panorama tecnológico atual, Instituto de Pesquisas Tecnológicas do Estado de São Paulo LOPO JOSÉ INFANTE DA CÂMARA LOPO CARVALHO (2010) Avaliação do potencial de produção de biogás a partir de biomassa proveniente de culturas dedicadas de ETARI, Instituto Superior de Agronomia Universidade Técnica de Lisboa DANIELE OLMETTO (2008) Codigestione anaerobica di fanghi di depurazione e frazione organica de R. U., Alma Mater Studiorum—Università di Bologna Facoltà di Ingegneria Corso di Laurea in Ingegneria per l'Ambiente e it Territorio—Tesi di Laurea in Ingegneria Sanitaria Ambientale LS b) Patents PATENTE MU 8502073-7U—Data de Depósito Sep. 16, 2005 Data de Publicação : May 29, 2007 (RPI 1899)

PATENTE PI01000529-3 A2—Data de Depósito Feb. 25, 2010 Data de Publicação : Oct. 18, 2011 (RPI 2128)

PATENTE PI0617206-7 A2—Data de Depósito Sep. 9, 2006 Data de Publicação : Jul. 19, 2011 (RPI 2115)

PATENTE PI 0600734-1 A—Data de Depósito Mar. 6, 2006 Data de Publicação : Nov. 20, 2007 (RPI 1924)

PATENTE PI 1000523 A2—Data de Depósito Feb. 25, 2010 Data de Publicação: Oct. 18, 2011 (RPI 2128)

EP 2248886 A2

U.S. Pat. No. 5,942,116

U.S. Pat. No. 4,274,838

US 2010/0159571A1

Problems

The main problems of the actual applications are listed below:

Solutions at points 1 and 2 above, involves raising costs for the nutrients or corn, in the latter case including longer retention times in the digesters.

Solution at point 3, which offers up to a 30% increase in production through the addition of alloctone bacteria and enzymes in the biomass in the digesters, entails a certain risk in terms of bio-security, to the extent that according to import-export rules we have restrictions and environmental authorities are reluctant to concede the related authorizations.

Solutions at point 4 have had reduced efficacy due to the little control of the biological balance and the lack of a process management specifically devoted to the optimization of biogas production.

Time for the completion of biodigestion process, on average 30/40 days, must be considered, entailing large volume of biodigesters in use, which must be equal to the volume of the daily biomass loaded multiplied for the number of days needed for the completion of the biodigestion process. We must consider, in fact, that the daily load at the input, passes through the biodigester to be finally removed from it, only after 30/40 days, as residual slurry that, once dehydrated, becomes compost. Apart from the increase of costs due to the dimension of a bigger biodigester, times of restarting in case of a stop must be considered and the additional costs in case of a restarting in a plant where this can be given only after the complete drainage of the digester.

Finally we must consider that generally solutions that give priority to the aspects related to the cutting down of polluting loads, in order to comply with legislation, end up producing a low quality compost, due to the presence of ill digested fractions.

Solutions in a General Way

The starting point is an inversion of classical approach to anaerobic biodigestion, which considers the disposal of polluting wastes as a priority. In this way, the process is directed mainly toward the cutting down of polluting charges of wastes, according to the existing laws, without paying too much attention to fully taking advantage of the energetic potential of those wastes that are being treated.

In this invention the priority is given to the full energetic potential of wastes, namely to a production of biogas and energy as high as possible. Considering the full energetic potential of wastes, an advanced management of the entire process becomes a priority, entailing the increase and stabilization of the quality and quantity of the biogas produced.

On the basis of any kind of organic waste and of its energetic potential, as related in scientific literature, research and field applications, the system invented make possible an increase and acceleration of the methanogenic process and its stabilization in time. For this aim, the system monitors the process in real time, considering its ongoing variations, based on previous recipes simulated for each case from the beginning, that consider the activity of methanogens in that specific process, the nutrients balance and other process variables as pH, temperature and so on. The system monitors and intervenes successively in the bacterial processes responsible for the methanogenesis, as well as in all the other physical-chemical variables of the process through a hardware-software system which accelerates and increases it, stabilizing at the same time the micro-biological activity.

The set biotechnological and computational components constitutes the essence of this invention: a process of biological cultures, developed thanks to a bio-accelerator, is integrated to the anaerobic biodigesters system by an Expert System that manages the hardware connection through a dedicated management software served by a recipes Database.

In the figures, 1 represents Organic Wastes, that feed the plant 2 represents Accumulation Mixer/Homogenizer; 3 represents Anaerobic Biodigester; 4 represents Acceleration Device (Booster); 5 represents Expert System; 6 represents Plant Automation and Control System; 7 represents Compost 8 represents WWTP and Slurry treatment Plant 9 represents Biogas; 10 represents Turbines or Motors; 11 represents Generator; 12 represents Treated Water Reactor; 13 represents Biogas Filter; 41 represents Watertight Tank; 42 represents Means for mixing, withdrawal and re-introduction of the load; 43 represents Means for the temperature control; 44 represents Means for the introduction of additives and nutrients; 45 represents Monitoring Sensors for: Pression (P), Methane Percentage (CH4), Biogas flow (biogas), Temperature (T), PPM of carbon, nitrogen and phosphorus (C:N:P), Acid-base degree (pH), Electrical conductivity (mS), Oxyreduction (Rdx), Turbidity (TU); 46 represents Means for biological sampling and analysis; 47 represents Reactors for chemical substances for pH control; 48 represents Methane storage Tank; 501 represents PLC Programmable Logic Controller and electric automation of the Acceleration Device (4); 502 represents Main Control Station; 503 represents Server of programmes and mathematical models; 504 represents Database Server; 505 represents Interface with Automation and Control System (6) of the whole plant 506 represents Connection and automation programme; 507 represents Monitoring Programmes; 508 represents Recipes elaboration programmes; 509 represents Input data for the Expert System; and 510 represents Database elaboration programmes.

In the figures, lines follow international conventions for functional schemes. In particular dotted lines and diagonal dotted lines represent electrical connections, lines with overlapped waves show gas path, continuous lines represent functional service connections. Fluxes of materials are represented by a thicker dotted line.

DETAILED DESCRIPTION OF THE INVENTION

Figure 1:
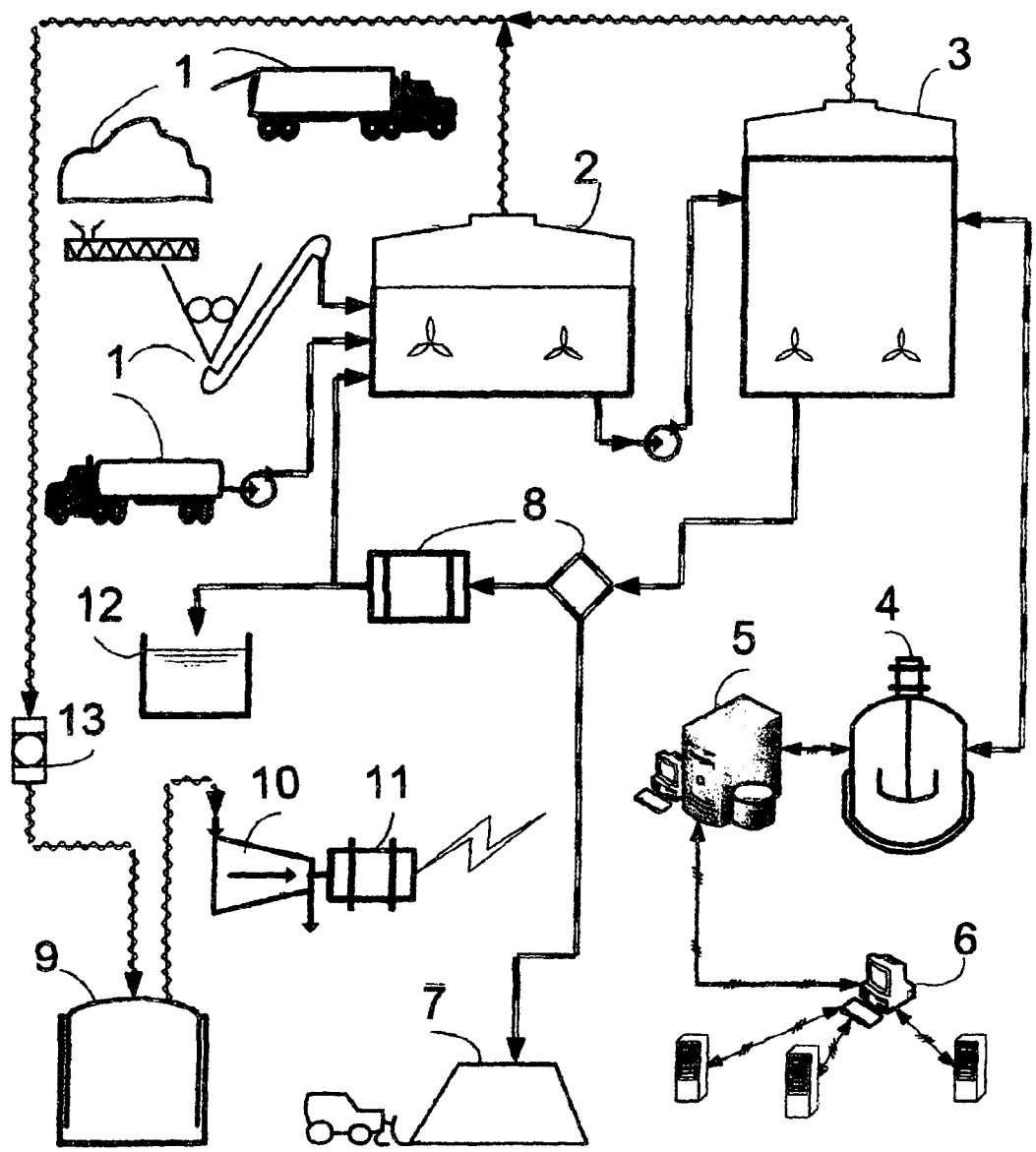
FIG. 1 is a diagram illustrating process of increasing biogas production, with high methane content, in anaerobic biodigestion plants according to an example embodiment of the present invention.

Referring to FIG. 1 Organic Wastes (1) are loaded in the Accumulation Mixer/Homogenizer (2), in order to homogenize the load and create an accumulation storage equal to 3 or 4 days of daily load, able to guarantee the continuous feeding of Anaerobic Biodigester (3), that will be of the type most appropriate to treat that kind of input Organic Wastes (1), even though having a reduction of total volume of about 30/40% less than digesters employed in traditional plants, as a result of the corresponding reduction of retention time of the process, made possible by the acceleration induced in the multiplication of methanogenic bacteria realized by the combined action of the Acceleration Device (4) and Expert System (5). In the Accumulation Mixer/Homogenizer (2) occurs the preliminary hydrolytic phase preceding successive acidogenic and methanogenic phases occurring inside the Anaerobic Biodigester (3).

From the Anaerobic Biodigester (3) we obtain, respectively, in the upper covering gas holder the Biogas (9) with high methane content and, in the outlet section, the Compost (7), after the separation of watery fraction.

Biogas (9), thus obtained, is purified from corrosive contaminants and refined by the Filter (13), before being sent to the motor or turbine (10) to operate the Generator (11). Water separated from Compost (7) that leaves the Anaerobic Digester (3) is treated by WWTP and Slurry treatment Plant (8) and stored in the Treated Water Tank (12).

Plant Automation and Control System (6), under the supervision of Expert System (5), provides to the automatic management of the plant.

Acceleration of the multiplication of methanogenic bacteria is realized according to the following sequence:

a) a fraction equal to K times the daily load of the Anaerobic Bio digester (3), collected in whatever manner, is sent to one or more Acceleration Devices (4) for the multiplication of autochthon methanogenic bacteria present in the Organic Wastes (1) and there it remains until the final concentration Cf of those bacteria be equal to M times the initial concentration Ci.

b) once obtained the final concentration Cf of methanogenic bacteria the collected fraction leaves the Accelerator Device (4) to be redirected to the Anaerobic Digester (3), preferably but not exclusively, in the inlet section of the same Anaerobic Digester (3), where it is mixed and distributed inside the whole lot of daily load.

c) Successive cycles of duration D of the above mentioned operations described at a) and b) are repeated, with K parameter assuming a value comprised between $10^{-3}$ and $10^{-1}$, with M parameter assuming a value comprised between $10^3$ and $10^7$ and with D parameter varying between 8 and 24 hours.

Figure 2:
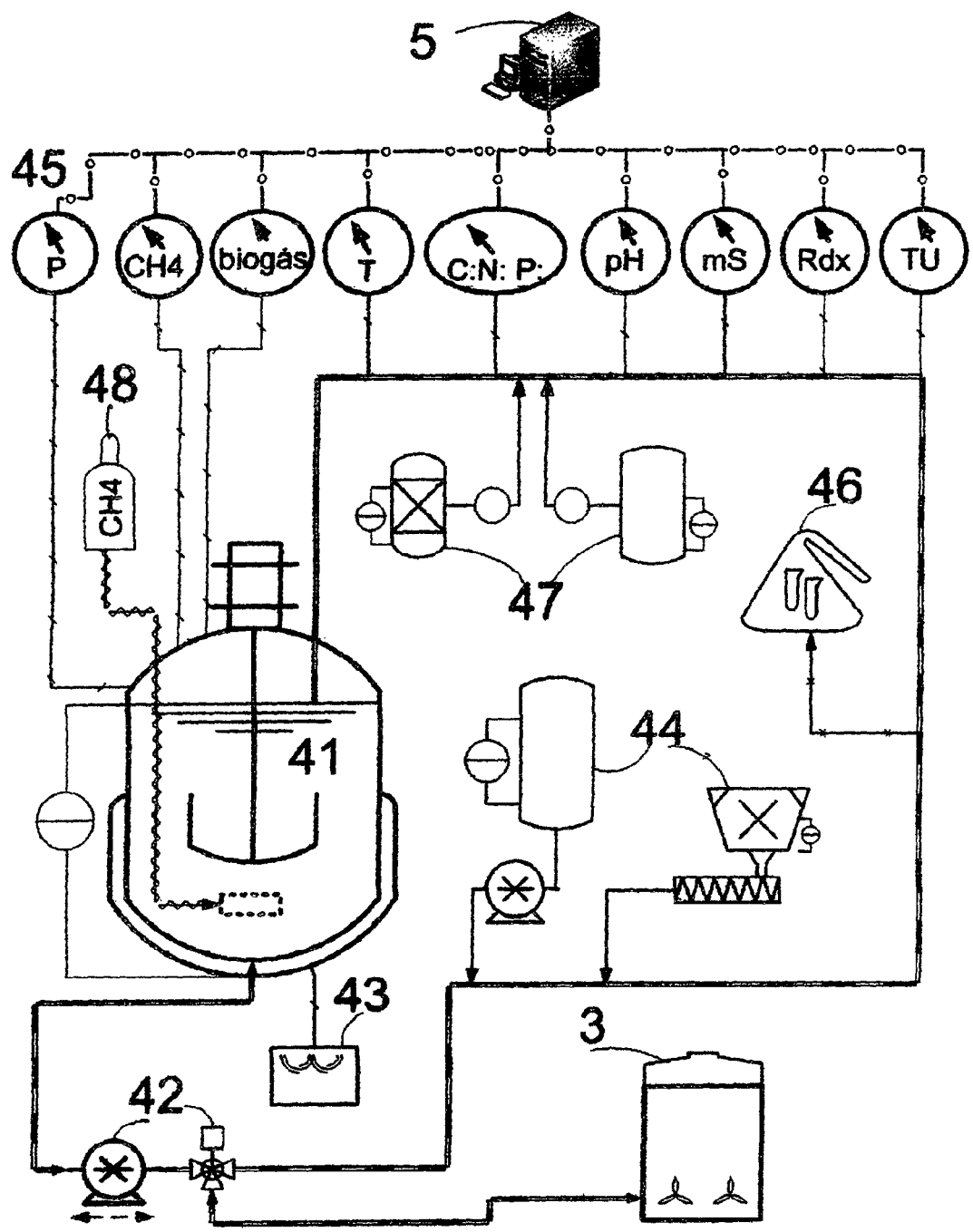
FIG. 2 is a diagram illustrating an acceleration device shown in FIG. 1.

In relation to FIG. 2, according to the invention, the Acceleration Device (4) is constituted by Watertight Tank (41), where a methane atmosphere is induced and where the following items are included:

a) Means for mixing, withdrawal and re-introduction of the load (42).

b) Means for the temperature control (43), such as to guarantee a temperature within the accelerator between 20° C. and 65° C.

c) Means for the introduction of additives and nutrients, such as to guarantee the balance of Carbon, Nitrogen and Phosphorus (44).

d) Means (45) for measuring and analyzing Temperature (T), Pression (P), Methane Percentage (CH4), Biogas flow (biogas), PPM of carbon, nitrogen and phosphorous (C:N:P), acid-basic degree (pH), Electrical conductivity (mS), Oxyreduction (Rdx) and Turbidity (TU)

e) Means for biological sampling and analysis (46), able to measure the bacteria development.

f) Tanks for chemical substances for pH control (47), between 5 and 8.

g) Methane storage Tank (48), which can be fed by the same biogas produced by the plant, previously filtered.

Operations, regulations, measurement and controls above mentioned and further on better detailed, are meant for the creation of a micro-environment ideal for the accelerated reproduction of autochthon methanogenic streams already present in the Organic Wastes (1).

As a matter of fact, by working with a reduced fraction (K) of the wastes to be treated, in a totally controlled environment, we make easier to drive the biological process in the desired direction. Let us consider, as an example, a medium size plant treating 100 ton/day of Organic Wastes (1), which sends to the Acceleration Device (4) a fraction K=1%, namely one tonne of Organic Wastes (1) which, having a density close to that of water, is equivalent to a cubic meter within the Acceleration Device (4). This is an easier environment to control if compared to the Anaerobic Digester (3) that, in the case of a traditional plant, would have a 3000 cubic meters volume (30 days×100 cubic meters per day), which is 3000 times more.

Through the Means for mixing (42), for PH Control (47) and Temperature control (43), hydrolysis as well as acidogenesis can be accelerated, that are phases preliminary to the disaggregation of complex molecules of proteins, fats and carbohydrates composing the Organic Wastes (1). Those phases are preliminary to the methanogenesis which occurs through the action of several methanogenic bacteria, that within the substrate find themselves in competition with other bacterial streams (aerobic, anaerobic and facultative), and that presents an original concentration Ci which is relatively low (some thousands per gram) into the Organic Wastes (1)

Thanks to the bubbling of methane coming from the Methane storage Tank (48), which is introduced counter flow the material being processed, and thanks to the addition of Nutrients (47) needed for the balance of Carbon, Nitrogen and Phosphorus (in a quantity 3000 times less than what would be needed to add to the traditional Anaerobic Biodigester (1) to obtain the same effect), we create an environment remarkably favourable to the development of existing autochthon methanogenic bacteria, that in these conditions can multiply themselves reaching the final concentration Cf close to one billion per gram in relatively short times, depending on the substrates used and on the environmental conditions created.

The control of the proliferation rate of the methanogenic streams is realized by a series of sensors (45) as abovementioned, along with the use of biological samplings and analysis (46), able to measure the bacteria development.

In our example with an initial concentration Ci=5000 bacteria per gram, detected by appropriate means of biological sampling and analysis (46), it can be deduced that through the Acceleration Device (4) a multiplication factor can be obtained equal to M=100.000.

Further on, keeping the same example, when our one ton of Organic Wastes (1), treated in the Acceleration Device (4), is re-directed to the Anaerobic Biodigester (3), preferably through the inlet section, getting mixed with the 99 tons already contained in it, the multiplication factor Mr is reduced to Mr=M×K=1000, meaning that autochthon methanogenic bacteria living in that load have become 1000 times more numerous in relation to the original concentration: this accelerates the Biogas (9) production, raising at the same time the percentage of methane contained in it.

At this stage new cycles of biomass withdrawal and successive re-introduction, once potentiated, are re-started with a D duration successively decreasing.

According to another version of this same invention fraction K of Organic Wastes (1) can be withdrawn also from the intermediate sections of the Anaerobic Biodigester (3) and re-directed, once potentiated, to the inlet section of the Anaerobic Biodigester (3) as much as to the other section: in this case duration D will be shorter.

Moreover, according to the invention, in the initial phase of the loading of the plant, fraction K of Organic Wastes (1), could be possibly withdrawn directly from the Accumulation Mixer/Homogenizer (2), to be successively re-introduced potentiated, to the same or to the inlet section of the Anaerobic Biodigester (3).

Figure 3:
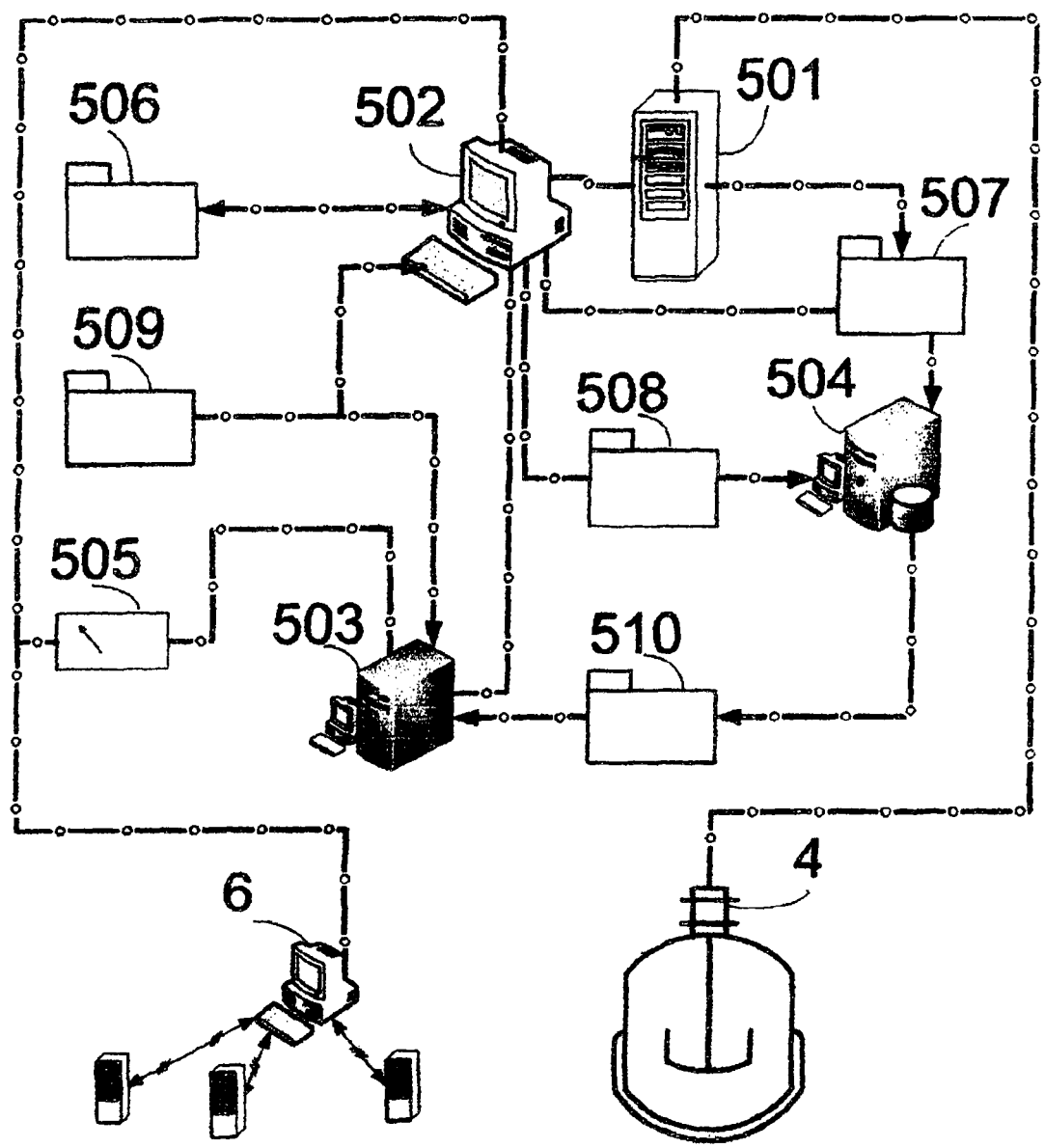
FIG. 3 is a diagram illustrating an Expert System, which controls the process of increasing biogas production, with high methane content, in anaerobic biodigestion plants.

In relation to FIG. 3, the sequence of operations related to the functioning of the Acceleration Device (4) is realized automatically through an Expert System composed of:

a) PLC Programmable Logic Controller and electric automation (501) of the Acceleration Device (4)

b) Main Control Station (502) where the supervision of the Acceleration Device (4) is realized, with the visualization of synoptical controls of the latter and of the whole plant through the Plant Automation and Control System (6).

c) Server of programmes and mathematical models (503), where all programmes related to the management development are installed.
d) Database Server (504), a database for the control of micro-environment of accelerated multiplication of the autochthon methanogenic bacteria.
e) Interface (505) with Automation and Control System (6) of the Anaerobic Biodigester (3) and of the whole plant.
f) Connection and automation programme (506), which allows connections with the different parts of the automation system.
g) Monitoring Programmes (507) which enables the online transformation, visualization and recording of process data.
h) Recipes elaboration programmes (508) that allows to elaborate in the Database recipes obtained from the evolution curves of parameters measured by instruments (45), subject to the dosing actuators, and also from laboratory data and data from other plants.
i) Input data for the Expert System (509), which can be local (via operator) or remote.
l) Database elaboration programmes (510) that manage data in the server and organize them in function of the demands of the above-mentioned programmes.

The architecture here described allows the complete control of the multiplication process of the autochthon methanogenic bacteria within the Acceleration Device (4).

Algorithms derived from the analysis of trends allow parameters, with the help of Fuzzy Logic modelling, to be directed automatically to the commands that comply to the necessities of the process.

Even on the basis of approximated input data, the system realize the auto-correction promoting automatically the variations the methanogenic process requires.

For example the system understands through recipes and mathematical models that multiplication is advancing if:
Turbidity raises
Ph between 5 and 6.8
Percentage of methane $CH_4$ rises
Biogas flux rises
Temperature is in the ideal range for that stage
Etc.

The Expert System (5) also controls, through the Main Control Station (502), the Automation and Control System (6) of the Plant through the Interface (505) with it, to force the alignment of parameters apt to the reproduction, inside the Anaerobic Biodigester (3), of the same micro-environment created inside the Acceleration Device (4), achieving the increase in biogas production (9) and in methane percentage contained in it.

The operator can follow the development of the process and of the automation on the screens of the Main Control Station (502).

In case of new situations occurring, not contemplated by actual software configuration, the operator will be able to manually intervene and the system will record the new operation automatically.

According to the present invention the Expert System (5) take advantage of the analysis and parameters detected during the monitoring of biodigestion process to formulate recipes for the correction of Compost (7) extracted from the Anaerobic Biodigester (3), in order to increase the fertilizing power.

According to the present invention the Expert System (5) take advantage of the analysis and parameters detected during the monitoring of biodigestion process in order to regulate the WWTP and Slurry treatment Plant (8), in order to turn more efficient the production of water entering the Treated Water Tank (12).

In FIG. 1, in order to facilitate the understanding, we did not represent the cooling circuits of Turbines or Motors (10), which allow the use of thermal energy, in cogeneration, for the appropriate heating of Anaerobic Biodigester (3) and, in trigeneration by heat pumps, to feed air conditioning systems.

Biogas (9) produced can also be treated to produce methane very similar to natural gas, what make possible a successive employment where natural gas is being employed, as for domestic, industrial or vehicular usages.

Finally, a plant according to the invention here put forward, starting from Organic Wastes (1), produces Electric Energy (11), thermal energy, Treated Water (12) and Compost (7) which can be easily turned into organic fertilizer and, if required, natural gas equivalent (biogas refined up to 97-99% $CH_4$ percentage). The reduction of biodigesters (−30%) dimensions reflects positively upon the reduction of costs, with a 10% increased performance in terms of biogas production, thanks to the accelerated biodigestion which takes a full advantage of volatile solids contained in each substrate. At the same time an extra 15% of methane contained in the biogas is achieved, upgrading the content of methane from the average $CH_4$ 60% of traditional plant to $CH_4=75\%$, in the case here presented.

The invention claimed is:

1. A process of increasing biogas (9) production, with high methane content, in anaerobic biodigestion plants, comprising:
   a) obtaining from an anaerobic biodigester (3) a fraction of organic waste equal in weight to K times the weight of the daily organic waste load of the anaerobic biodigester (3), wherein the parameter K is a numeric value selected between $10^{-3}$ and $10^{-1}$, sending the fraction to one or more acceleration devices (4) within which a micro-environment ideal for the accelerated multiplication of methanogenic bacteria contained in the organic wastes (1) is established by introducing additives and nutrients, retaining the fraction in the one or more acceleration devices (4) until a final concentration (Cf) of the methanogenic bacteria in the fraction is equal to M times an initial concentration (Ci), wherein the parameter M is a numeric value selected between $10^3$ and $10^7$;
   b) as soon as said final concentration (Cf) is obtained in the fraction, directing said fraction from the acceleration device (4) back to the anaerobic biodigester (3); and
   c) successively repeating steps a) and b), wherein an operation duration D of each cycle for performing steps a) and b) is gradually reduced from approximately 24 hours to approximately 8 hours.

2. The process according to claim 1, wherein the acceleration device (4) includes:
   a watertight tank (41) within which the fraction of organic waste withdrawn from the anaerobic digester (3) is treated to accelerate multiplication of methanogen concentrations to reach the final concentration Cf;
   means (42) for mixing, withdrawal from the anaerobic digester (3), and re-introduction to the anaerobic digester (3) of a fraction of organic waste equal in weight to K times the weight of the daily organic waste load of the anaerobic biodigester;
   means for the temperature control (43) of the environment within the watertight tank;

means (44) for the introduction of additives and nutrients to the watertight tank;

monitoring means (45) including monitoring sensors for measurement and analysis of temperature (T), pressure (P), percentage of methane (CH4), biogas flow (biogas), ppm of carbon, nitrogen and phosphorus (C:N:P), acid-basic degree (pH), electrical conductivity (mS), redox (Rdx) and turbidity (TU) within the watertight tank;

means for biological sampling and analysis (46) able to measure the development of bacteria in materials being processed within the watertight tank;

means for introduction of chemical substances for pH control (47) of the environment within the watertight tank;

a methane storage tank (48);

means of analysis to identify optimal combinations of parameters for accelerating production of the methanogenic bacteria through analysis of data from operations of the means for the temperature control (43), means (44) for the introduction of additives and nutrients, monitoring means (45), means for biological sampling and analysis (46), and means for introduction of chemical substances for pH control (47); and means for sending data regarding the optimal parameters to the control system of the anaerobic biodigester (3).

3. The process according to claim 2, further comprising: introducing methane into the watertight tank of the acceleration device (4) from methane storage tank (48) and bubbling it through the material being processed in the watertight tank.

4. The process according to claim 1, wherein the anaerobic biodigester (3) includes an inlet section, through which the daily organic waste load of the anaerobic biodigester (3) is transported into the anaerobic biodigester (3), and from which the fraction of organic waste equal in weight to K times the weight of the daily organic waste load of the anaerobic biodigester (3) is removed and sent to the one or more acceleration device (4) for treatment in the watertight tank, after which treatment, the fraction of organic waste having attained the pre-decided final concentration (Cf) of the methanogenic bacteria, is removed from the watertight tank and is directed from the acceleration device (4), back to the anaerobic biodigester (3) through the same inlet section of the anaerobic biodigester (3).

5. The process according to claim 1, wherein the anaerobic biodigester (3) includes intermediate sections, through which the fraction of organic waste is directed from the acceleration device (4) back to the anaerobic biodigester (3) after the fraction of organic waste having the pre-decided final concentration (Cf) of the methanogenic bacteria is obtained in the one or more acceleration device (4).

* * * * *